US012742842B2

(12) United States Patent
Ishii et al.

(10) Patent No.: US 12,742,842 B2
(45) **Date of Patent: *Sep. 22, 2026**

(54) PATIENT TABLE AND MAGNETIC RESONANCE IMAGING APPARATUS

(71) Applicant: FUJIFILM Corporation, Tokyo (JP)

(72) Inventors: Koki Ishii, Tokyo (JP); Atsushi Ota, Tokyo (JP); Takashi Chuman, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 19/230,859

(22) Filed: Jun. 6, 2025

(65) Prior Publication Data

US 2025/0375335 A1 Dec. 11, 2025

(30) Foreign Application Priority Data

Jun. 7, 2024 (JP) ................................ 2024-092782

(51) Int. Cl.
*G01R 33/36* (2006.01)
*A61B 5/00* (2006.01)
*A61B 5/055* (2006.01)
*G01R 33/28* (2006.01)
*G01R 33/30* (2006.01)

(52) U.S. Cl.
CPC .......... *G01R 33/3692* (2013.01); *A61B 5/055* (2013.01); *A61B 5/704* (2013.01); *G01R 33/307* (2013.01); *G01R 33/283* (2013.01)

(58) Field of Classification Search
CPC ......................... G01R 33/3692; G01R 33/307; G01R 33/283; A61B 5/055; A61B 5/704
See application file for complete search history.

(56) References Cited

U.S. PATENT DOCUMENTS 7,173,426 B1 2/2007 Bulumulla et al.
12,097,057 B1 9/2024 Gelbien
(Continued)

FOREIGN PATENT DOCUMENTS

CN 114252826 A * 3/2022 ............. A61B 5/055
EP 302 694 A1 1/2024
(Continued)

OTHER PUBLICATIONS

The extended European search report issued by the European Patent Office on Feb. 23, 2026, which corresponds to European Patent Application No. 25181153.5-1122 and is related to U.S. Appl. No. 19/230,859.

(Continued)

*Primary Examiner* — Carolyn A Pehlke
(74) *Attorney, Agent, or Firm* — Studebaker Brackett PLLC

(57) ABSTRACT

A patient table includes: a movable top plate; a leg portion that supports the top plate; a signal conversion unit that is disposed inside the top plate and includes an A/D converter and an electrical-to-optical converter which convert a signal obtained from a receive coil unit into an optical signal; an optical cable that transmits the optical signal output from the signal conversion unit; and an optical wireless unit that is disposed on the leg portion, that is connected to the optical cable, and that transmits the optical signal via optical wireless communication, in which the optical wireless unit is disposed at a position that is hidden beneath the top plate in a case where the top plate is at an initial position before moving into an imaging space and that is exposed on the leg portion as the top plate moves into the imaging space.

16 Claims, 12 Drawing Sheets

(56) References Cited

U.S. PATENT DOCUMENTS

2006/0058639 A1 3/2006 Izuhara et al.
2015/0168513 A1 6/2015 Mori et al.
2016/0077175 A1 3/2016 Mori
2018/0003791 A1 1/2018 Kimmlingen et al.
2021/0030306 A1 2/2021 Leussler et al.
2022/0265496 A1 8/2022 Xue et al.
2022/0322958 A1* 10/2022 Guan ..................... A61B 5/055
2024/0342027 A1 10/2024 Harrison et al.
2025/0375163 A1* 12/2025 Ishii ....................... A61B 5/704
2026/0007366 A1 1/2026 Leussler et al.

FOREIGN PATENT DOCUMENTS

JP 2007-144192 A 6/2007
JP 2009 240660 A 10/2009
JP 20140-61282 A 4/2014
JP 2014-230610 A 12/2014
WO WO-2009150575 A1 * 12/2009 ......... G01R 33/3692

OTHER PUBLICATIONS

The partial European search report (R. 64 EPC) issued by the European Patent Office on Oct. 24, 2025, which corresponds to European Patent Application No. 25181153.5-1122 and is related to U.S. Appl. No. 19/230,859.

The extended European search report issued by the European Patent Office on Oct. 29, 2025, which corresponds to European Patent Application No. 25181167.5-1122 and is related to U.S. Appl. No. 19/230,859.

A Non-Final Office Action mailed by the United States Patent and Trademark Office on Apr. 29, 2026, which corresponds to U.S. Appl. No. 19/230,859, and is related to U.S. Appl. No. 19/230,859.

* cited by examiner

FIG. 2

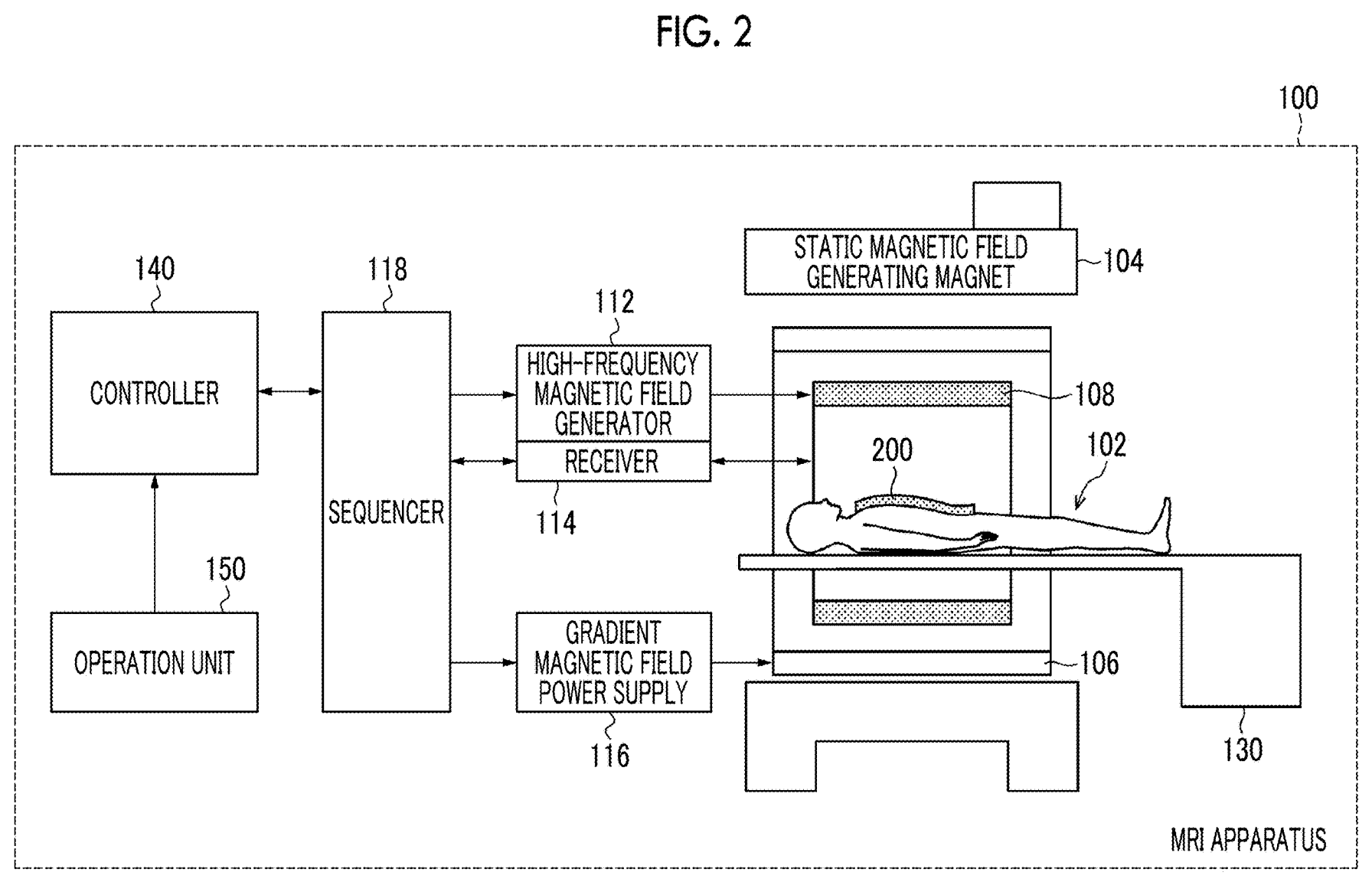

100
MRI APPARATUS
STATIC MAGNETIC FIELD GENERATING MAGNET
104
108
102
106
130
200
HIGH-FREQUENCY MAGNETIC FIELD GENERATOR
112
RECEIVER
114
GRADIENT MAGNETIC FIELD POWER SUPPLY
116
SEQUENCER
118
CONTROLLER
140
OPERATION UNIT
150

MACHINE ROOM
MRI ROOM
IMAGE RECONSTRUCTION UNIT
CONTROL UNIT
146
142
152
312
310
50
10
136-2
130
130A
130B
132-2
110
220
200
102
134-2
136-1
134-1
104
108
132-1
106

200
RECEIVE COIL UNIT
134-2
A/D CONVERSION UNIT
10
40-1
O/E
E/O
42-1
44
P/S
46
OPTICAL WIRELESS TRANSMISSION UNIT
RECEIVE COIL UNIT
205
A/D CONVERSION UNIT
134-3
40-2
O/E
E/O
42-2
S/P
48
OPTICAL WIRELESS RECEPTION UNIT
47

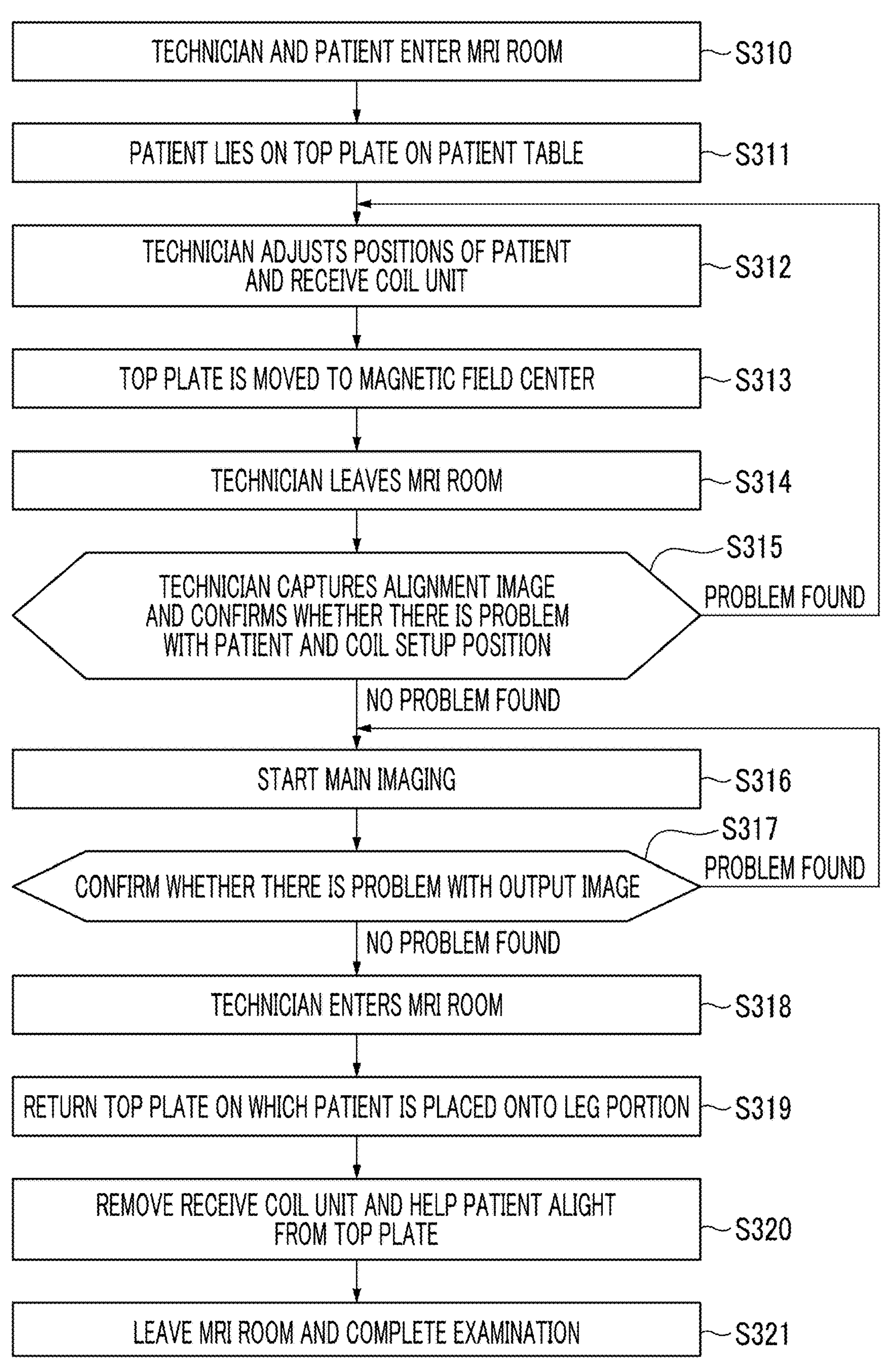
FIG. 11
TECHNICIAN AND PATIENT ENTER MRI ROOM
S310
PATIENT LIES ON TOP PLATE ON PATIENT TABLE
S311
TECHNICIAN ADJUSTS POSITIONS OF PATIENT AND RECEIVE COIL UNIT
S312
TOP PLATE IS MOVED TO MAGNETIC FIELD CENTER
S313
TECHNICIAN LEAVES MRI ROOM
S314
S315
TECHNICIAN CAPTURES ALIGNMENT IMAGE AND CONFIRMS WHETHER THERE IS PROBLEM WITH PATIENT AND COIL SETUP POSITION
PROBLEM FOUND
NO PROBLEM FOUND
START MAIN IMAGING
S316
S317
CONFIRM WHETHER THERE IS PROBLEM WITH OUTPUT IMAGE
PROBLEM FOUND
NO PROBLEM FOUND
TECHNICIAN ENTERS MRI ROOM
S318
RETURN TOP PLATE ON WHICH PATIENT IS PLACED ONTO LEG PORTION
S319
REMOVE RECEIVE COIL UNIT AND HELP PATIENT ALIGHT FROM TOP PLATE
S320
LEAVE MRI ROOM AND COMPLETE EXAMINATION
S321

PARALLEL
OPTICAL
COMMUNICATION
50-1
50-2
10-1
10-2
130B
136-2
136-3
132-2
132-3
220
136-4
200
206
136-1
226
132-1
132-4
130A
102

PATIENT TABLE AND MAGNETIC RESONANCE IMAGING APPARATUS

CROSS-REFERENCE TO RELATED APPLICATION

The present application claims priority under 35 U.S.C. § 119(a) to Japanese Patent Application No. 2024-092782 filed on Jun. 7, 2024, which is hereby expressly incorporated by reference, in its entirety, into the present application.

BACKGROUND OF THE INVENTION

1. Field of the Invention

The present disclosure relates to a patient table and a magnetic resonance imaging (MRI) apparatus.

2. Description of the Related Art

In an MRI apparatus, a subject placed in a static magnetic field is irradiated with high-frequency electromagnetic waves to excite nuclear spins inside the subject, for example, nuclear spins of hydrogen atoms, and nuclear magnetic resonance (NMR) signals generated in a case where the excited nuclear spins return to an equilibrium state is detected and subjected to signal processing, thereby visualizing a distribution of hydrogen atomic nuclei inside a living body as an image.

JP2014-61282A describes a magnetic resonance imaging apparatus comprising: a patient table on which a subject is placed; a gantry portion that supports a static magnetic field magnet and a gradient magnetic field coil; a receive coil unit that receives a magnetic resonance signal emitted from the subject; a conversion unit that converts the magnetic resonance signal output from the receive coil unit into a digital signal to generate magnetic resonance signal data; and a collection unit that collects the magnetic resonance signal data, in which the patient table or the gantry portion includes a coil port that connects the receive coil unit and the collection unit, and the conversion unit is provided on the coil port or a relay unit that relays between the receive coil unit and the coil port.

JP2014-230610A describes a magnetic resonance imaging apparatus including a patient table unit on which a subject is placed, the magnetic resonance imaging apparatus comprising: a digital processing unit that is disposed inside the patient table unit and that acquires an analog nuclear magnetic resonance signal from a receive coil unit, which detects a nuclear magnetic resonance signal emitted from the subject, and that digitizes the nuclear magnetic resonance signal; a first wireless communication unit that wirelessly transmits the nuclear magnetic resonance signal digitized by the digital processing unit; a second wireless communication unit that receives the nuclear magnetic resonance signal wirelessly transmitted by the first wireless communication unit; and an image reconstruction unit that reconstructs image data based on the nuclear magnetic resonance signal received by the second wireless communication unit.

JP2007-144192A describes a magnetic resonance imaging system comprising: a plurality of coil elements configured to supply each coil output signal based on a plurality of magnetic resonance response signals detected by the coil elements; and an optical link coupled to the plurality of coil elements in order to transmit at least one optical beam configured to transmit receive coil signal information through the air.

SUMMARY OF THE INVENTION

Conventionally, weak magnetic resonance signals acquired by the receive coil unit have been transmitted via electrical cables and digitized at a position away from a gantry. Since analog transmission of signals raises concerns about noise interference and signal loss, a configuration has been proposed in which the signals are digitized inside a top plate close to the receive coil unit (JP2014-61282A and JP2014-230610A). In addition, since the MRI apparatus generates electromagnetic waves due to radio frequency (RF) irradiation in a strong magnetic field environment, using optical wireless communication with a frequency different from the RF irradiation frequency is effective for making the signal transmission, such as the nuclear magnetic resonance signals acquired by the receive coil unit, cable-free (JP2007-144192A). By converting the digitized signals into optical wireless signals inside the top plate, radio wave interference with the MRI apparatus can be avoided.

However, there is a concern that optical wireless communication may cause communication failure in a case where the communication is obstructed by an object or dust.

The present disclosure has been made in view of such circumstances, and an object of the present disclosure is to provide a patient table and a magnetic resonance imaging apparatus capable of suppressing communication failure caused by dust or the like and realizing stable optical wireless communication.

According to a first aspect of the present disclosure, there is provided a patient table comprising: a top plate that moves with a subject placed thereon; a leg portion that supports the top plate; a signal conversion unit that is connected to a receive coil unit which receives a signal generated by the subject, the signal conversion unit being disposed inside the top plate and including an A/D converter that converts the signal obtained from the receive coil unit into a digital signal, and an electrical-to-optical converter that converts the digital signal into an optical signal; an optical cable that is disposed inside the top plate and the leg portion and that transmits the optical signal output from the signal conversion unit; and an optical wireless unit that is disposed on the leg portion, that is connected to the optical cable, and that transmits the optical signal via optical wireless communication, in which the optical wireless unit is disposed at a position that is hidden beneath the top plate in a case where the top plate is at an initial position before moving into an imaging space and that is exposed on the leg portion as the top plate moves into the imaging space.

With the patient table according to the first aspect, in a case where the top plate is at the initial position, the optical wireless unit is located beneath the top plate, and the optical wireless unit is covered by the top plate, that is, is in a non-exposed state. Consequently, it is possible to suppress the adhesion of dust or the like to the optical wireless unit. In a case where the top plate moves from the initial position into the imaging space, the optical wireless unit is exposed on the leg portion, thereby enabling optical wireless communication. According to the first aspect, it is possible to suppress communication failure caused by dust or the like and realize stable optical wireless communication.

In addition, according to the first aspect, the signal obtained from the receive coil unit is digitized by the signal conversion unit inside the top plate, converted into an optical signal, and transmitted, thereby enabling data transmission while suppressing noise interference and signal loss.

According to a second aspect, in the patient table according to the first aspect, a configuration may be employed in which the optical wireless unit is disposed on an upper surface portion of the leg portion.

According to a third aspect, in the patient table according to the first or second aspect, a configuration may be employed in which the optical wireless unit is disposed on an upper surface portion of the leg portion at an end portion on a side opposite to the imaging space.

According to a fourth aspect, in the patient table according to any one of the first to third aspects, a configuration may be employed in which the top plate includes a coil port including a connector to which a signal transmission cable of the receive coil unit is connected, and the signal conversion unit is disposed to correspond to the coil port.

According to a fifth aspect, in the patient table according to the fourth aspect, a configuration may be employed in which the top plate includes a plurality of the coil ports, and the signal conversion unit is provided for each of the plurality of coil ports.

According to a sixth aspect, in the patient table according to any one of the first to fifth aspects, a configuration may be employed in which a plurality of the signal conversion units and a plurality of the optical cables are provided.

According to a seventh aspect, in the patient table according to the sixth aspect, a configuration may be employed in which the optical wireless unit includes a switch for selecting a signal to be activated from the plurality of signal conversion units.

According to an eighth aspect, in the patient table according to the sixth or seventh aspect, a configuration may be employed in which the optical wireless unit includes a circuit that serializes signals obtained from a plurality of the receive coil units connected to the plurality of signal conversion units.

According to a ninth aspect, in the patient table according to any one of the first to eighth aspects, a configuration may be employed in which the signal conversion unit includes a digital processing circuit.

According to a tenth aspect, in the patient table according to the ninth aspect, a configuration may be employed in which the digital processing circuit includes a decimator that thins out digitized data.

According to an eleventh aspect, in the patient table according to the ninth or tenth aspect, a configuration may be employed in which the digital processing circuit includes a circuit that performs encoding.

According to a twelfth aspect, in the patient table according to any one of the first to eleventh aspects, a configuration may be employed in which a plurality of the optical wireless units are provided.

According to a thirteenth aspect, in the patient table according to any one of the first to twelfth aspects, a configuration may be employed in which a sensor that detects movement of the top plate; and a first circuit that operates the optical wireless unit based on a signal obtained from the sensor are further provided.

According to a fourteenth aspect, in the patient table according to the thirteenth aspect, a configuration may be employed in which the first circuit includes a circuit that turns ON/OFF power of the optical wireless unit.

According to a fifteenth aspect, in the patient table according to any one of the first to fourteenth aspects, a configuration may be employed in which the top plate includes a weight sensor that detects a boarding and alighting state of the subject, and the patient table further comprises a second circuit that operates the optical wireless unit based on a signal obtained from the weight sensor.

According to a sixteenth aspect, in the patient table according to the fifteenth aspect, a configuration may be employed in which the second circuit includes a circuit that turns ON/OFF power of the optical wireless unit.

According to a seventeenth aspect of the present disclosure, there is provided a magnetic resonance imaging apparatus comprising: the patient table according to any one of the first to sixteenth aspects; a gantry that generates a static magnetic field, a gradient magnetic field, and a high-frequency magnetic field in an imaging space; a second optical wireless unit that performs optical wireless communication with a first optical wireless unit which is the optical wireless unit; and an image reconstruction unit that reconstructs an image based on data of a nuclear magnetic resonance signal acquired via the second optical wireless unit.

With the magnetic resonance imaging apparatus according to the seventeenth aspect, the influence of noise components can be suppressed, thereby obtaining a high-quality image.

According to an eighteenth aspect, in the magnetic resonance imaging apparatus according to the seventeenth aspect, a configuration may be employed in which the second optical wireless unit is disposed on a ceiling or a wall of a room where the gantry is disposed.

According to a nineteenth aspect, in the magnetic resonance imaging apparatus according to the eighteenth aspect, a configuration may be employed in which the second optical wireless unit communicates with the first optical wireless unit via visible light communication and also serves as a light for the room.

According to a twentieth aspect, in the magnetic resonance imaging apparatus according to any one of the seventeenth to nineteenth aspects, a configuration may be employed in which a plurality of the second optical wireless units are provided.

According to a twenty-first aspect, in the magnetic resonance imaging apparatus according to any one of the seventeenth to twentieth aspects, a configuration may be employed in which a camera that monitors the subject on the top plate; and a third circuit that operates the first optical wireless unit based on information obtained from an image captured by the camera are further provided.

According to a twenty-second aspect, in the magnetic resonance imaging apparatus according to the twenty-first aspect, a configuration may be employed in which the third circuit includes a circuit that turns ON/OFF power of the first optical wireless unit in a case where a state in which the subject or a phantom is placed on the top plate is detected from the image captured by the camera.

With the patient table of the present disclosure, it is possible to suppress communication failure caused by dust or the like and realize stable optical wireless communication. In addition, with the magnetic resonance imaging apparatus of the present disclosure, the influence of noise components can be suppressed, thereby obtaining a high-quality image.

BRIEF DESCRIPTION OF THE DRAWINGS

FIG. 2 is a schematic diagram showing an internal configuration of the MRI apparatus.

FIG. 5 is a plan view of the patient table.

FIG. 7 is an explanatory diagram of bidirectional optical wireless communication using an optical wireless unit.

FIG. 9 is a plan view showing an example of a case where a plurality of receive coil units are connected to coil ports.

FIG. 11 is a flowchart showing a procedure of MRI imaging.

DESCRIPTION OF THE PREFERRED EMBODIMENTS

Figure 1:
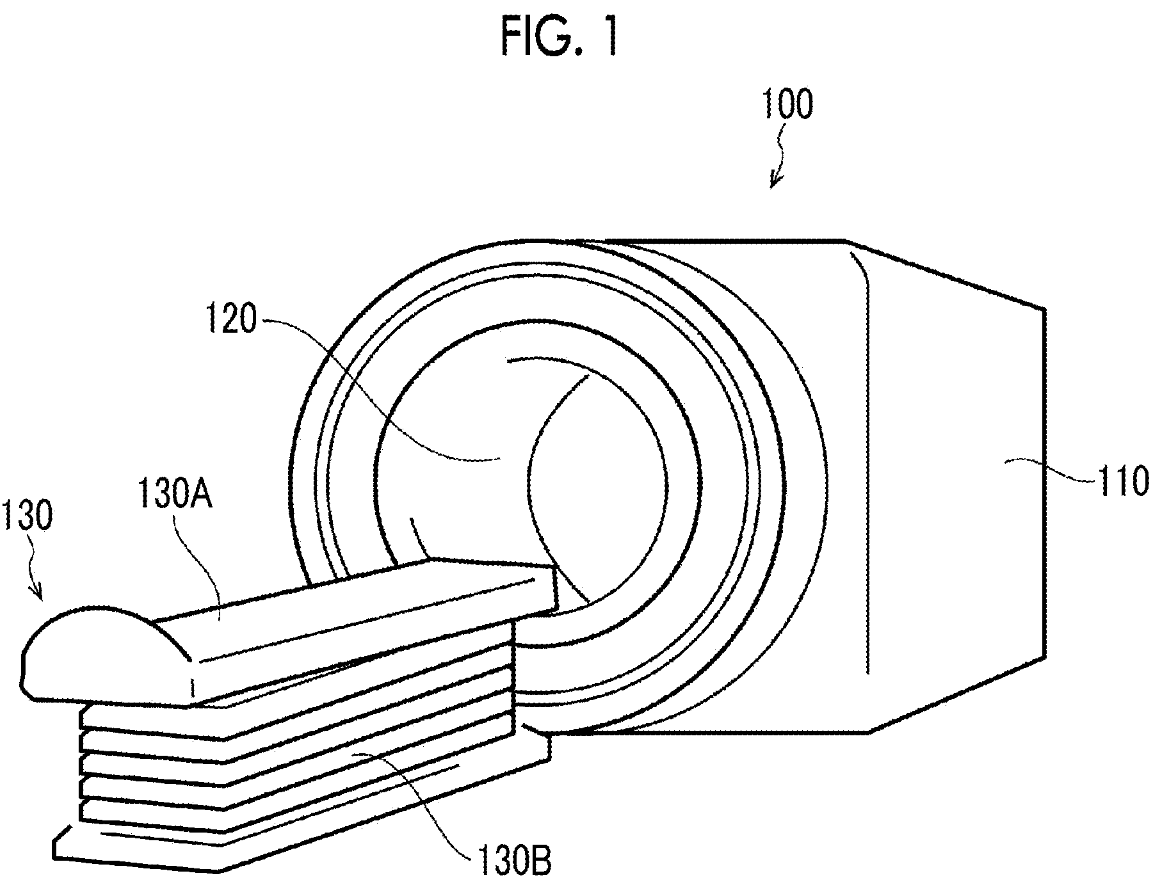
FIG. 1 is a perspective view showing an external appearance of an exemplary magnetic resonance imaging (MRI) apparatus.

Preferred embodiments of the present invention will be described in detail below with reference to the accompanying drawings. In the following description and the accompanying drawings, components having the identical functional configuration will be denoted by the identical reference numerals, and repetitive descriptions will not be repeated.

Overview of Magnetic Resonance Imaging (MRI) Apparatus

FIG. 1 is a perspective view showing an external appearance of an exemplary MRI apparatus 100. The MRI apparatus 100 comprises a gantry 110 which is an apparatus main body, and a patient table 130. The patient table 130 comprises a top plate 130A and a leg portion 130B that supports the top plate 130A, and is disposed in front of a bore 120, which is a cylindrical imaging space provided in the gantry 110. The top plate 130A can be moved into the bore 120 and moved out of the bore 120 by a top plate drive mechanism (not shown) provided in the leg portion 130B. The patient table 130 may be fixed to the gantry 110 or may be a movable patient table (dockable patient table) that is attachable to and detachable from the gantry 110.

FIG. 2 is a diagram showing a schematic configuration of an inside of the MRI apparatus 100. The MRI apparatus 100 comprises a static magnetic field generating magnet 104, a gradient magnetic field coil 106, a radio frequency (RF) transmit coil 108, and a receive coil unit 200. A subject 102 is placed on the top plate 130A of the patient table 130 and is disposed in the imaging space. That is, by moving the top plate 130A on which the subject 102 is placed to the bore 120, an examination site of the subject 102 is moved to be located at the center of a static magnetic field in the bore 120.

The static magnetic field generating magnet 104 generates a uniform static magnetic field in the imaging space. The static magnetic field generating magnet 104 includes a static magnetic field generating source of a permanent magnet type, a normal conducting type, or a superconducting type. The gradient magnetic field coil 106 generates a gradient magnetic field in the imaging space. The gradient magnetic field coil 106 is composed of gradient magnetic field coils in three-axis directions of X, Y, and Z in a real space coordinate system (stationary coordinate system). Each gradient magnetic field coil is connected to a gradient magnetic field power supply 116 and is supplied with a current. As a result, the gradient magnetic field is generated in the three-axis directions of X, Y, and Z.

The RF transmit coil 108 is a coil that irradiates the subject 102 with a high-frequency magnetic field pulse (RF pulse). The RF transmit coil 108 is connected to a high-frequency magnetic field generator 112 and is supplied with a high-frequency pulse current. The high-frequency magnetic field generator 112 is driven in accordance with a command from a sequencer 118, modulates the amplitude of a high-frequency pulse, and supplies the amplified high-frequency pulse to the RF transmit coil 108.

The sequencer 118 transmits commands to the high-frequency magnetic field generator 112 and the gradient magnetic field power supply 116 in accordance with an imaging pulse sequence to generate the high-frequency magnetic field and the gradient magnetic field, respectively. The generated high-frequency magnetic field is applied to the subject 102 as a pulsed high-frequency magnetic field (RF pulse) through the RF transmit coil 108. As a result, nuclear magnetic resonance (NMR) phenomena are induced in the spins of atoms that constitute biological tissues of the subject 102.

The receive coil unit 200 is a coil that receives echo signals (referred to as NMR signals) emitted by the NMR phenomena of the spins of atoms that constitute the biological tissues of the subject 102. In FIG. 2, an example of a blanket-type receive coil unit 200 applied to imaging of a chest and an abdomen is shown; however, a form of the receive coil unit may be applied differently depending on the examination site. For example, receive coil units for imaging various sites, such as a head, a spine, an abdomen, a leg, and an arm, can be used. The number of receive coil units used for a single imaging operation may be one or plural, and a plurality of receive coil units for imaging different sites may be used at the same time. The receive coil unit may be simply called a receive coil. The NMR signal generated from the subject 102 is received by the receive coil unit 200 and is subjected to A/D conversion by a receiver 114.

Demodulation is performed.

The sequencer 118 controls each unit to operate at a pre-programmed timing and intensity. Among programs, a program that particularly describes the timing and intensity of RF pulses, gradient magnetic fields, and signal reception is called a pulse sequence. Various pulse sequences are known depending on the purpose, but a detailed description thereof will be omitted here.

A controller 140 controls the operation of the MRI apparatus 100 via the sequencer 118 and receives a signal from the receiver 114 to perform various types of signal processing, such as image reconstruction. The receiver 114 converts the signal obtained from the receive coil unit 200 into raw data and then transmits the raw data to the controller 140, and the raw data is also referred to as the echo signal or measurement data.

The controller 140 can be configured using a computer. The computer applied to the controller 140 may be a personal computer or a workstation.

The controller 140 accepts various instruction inputs from an operation unit 150 to perform overall control of the units of the MRI apparatus 100 and to perform processing of converting the echo signal in a spatial frequency domain received via the sequencer 118 into a real-space image through inverse Fourier transformation, and the like, thereby generating an MRI image.

The operation unit 150 includes a mouse, a keyboard, and the like and functions as a part of a graphical user interface (GUI) that accepts an input from an operator using a display operation window of a display (not shown). That is, the operation unit 150 and the display function as the GUI for the operator to start and stop (pause) the MRI apparatus 100, select pulse sequences, and input imaging conditions, processing conditions, and the like.

Overview of Receive Coil Unit

Figure 3:
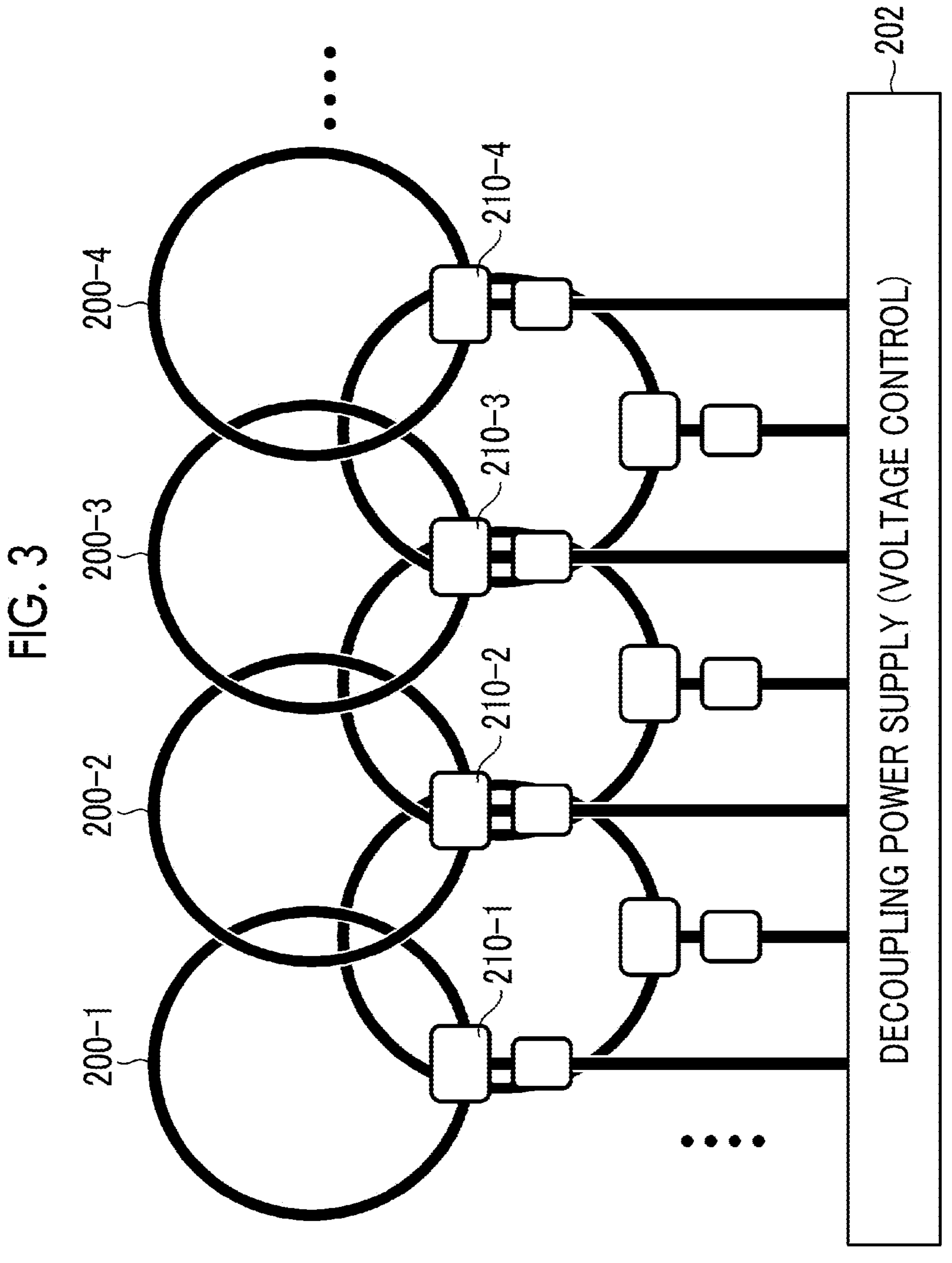
FIG. 3 is an overview diagram showing a configuration example of a receive coil unit.

FIG. 3 is an overview diagram showing a configuration example of the receive coil unit 200. The receive coil unit 200 may be, for example, a flexible, thin, and lightweight coil unit capable of covering a wide imaging range of the chest and the abdomen of the subject 102. The receive coil unit 200 is a multi-channel array coil. In the receive coil unit 200, a plurality of loop-shaped coil elements 200-1, 200-2, 200-3, 200-4, . . . , and **200-*n* that function as antennas that receive the NMR signals are disposed in a two-dimensional array, and decoupling circuits 210-1, 210-2, 210-3, 210-4, . . . , and 210-*n* are provided to correspond to the respective coil elements 200-*j*** (j=1, 2, 3, 4, . . . , and n).

Each of the plurality of coil elements **200-*j* functions as an antenna that receives the NMR signal generated from the biological tissue of the subject 102. Each coil element 200-*j*** is adjusted to resonate at a specific frequency. The specific frequency is determined by the atomic nucleus (typically, a hydrogen atomic nucleus) to be observed in the biological tissue and the magnetic field intensity.

The shape, the number (the number of channels), and the disposition form of the coil element **200-*j* are not limited to the example shown in FIG. 3. In a case of a receive coil unit for the abdomen, the number of coil elements 200-*j*** may range, for example, from 16 to 128.

The plurality of decoupling circuits **210-*j* (j=1, 2, 3, 4, . . . , and n) include voltage-driven field effect transistors (FETs), and the FET in each decoupling circuit is controlled ON/OFF by a drive voltage supplied from a decoupling power supply 202**.

Figure 4:
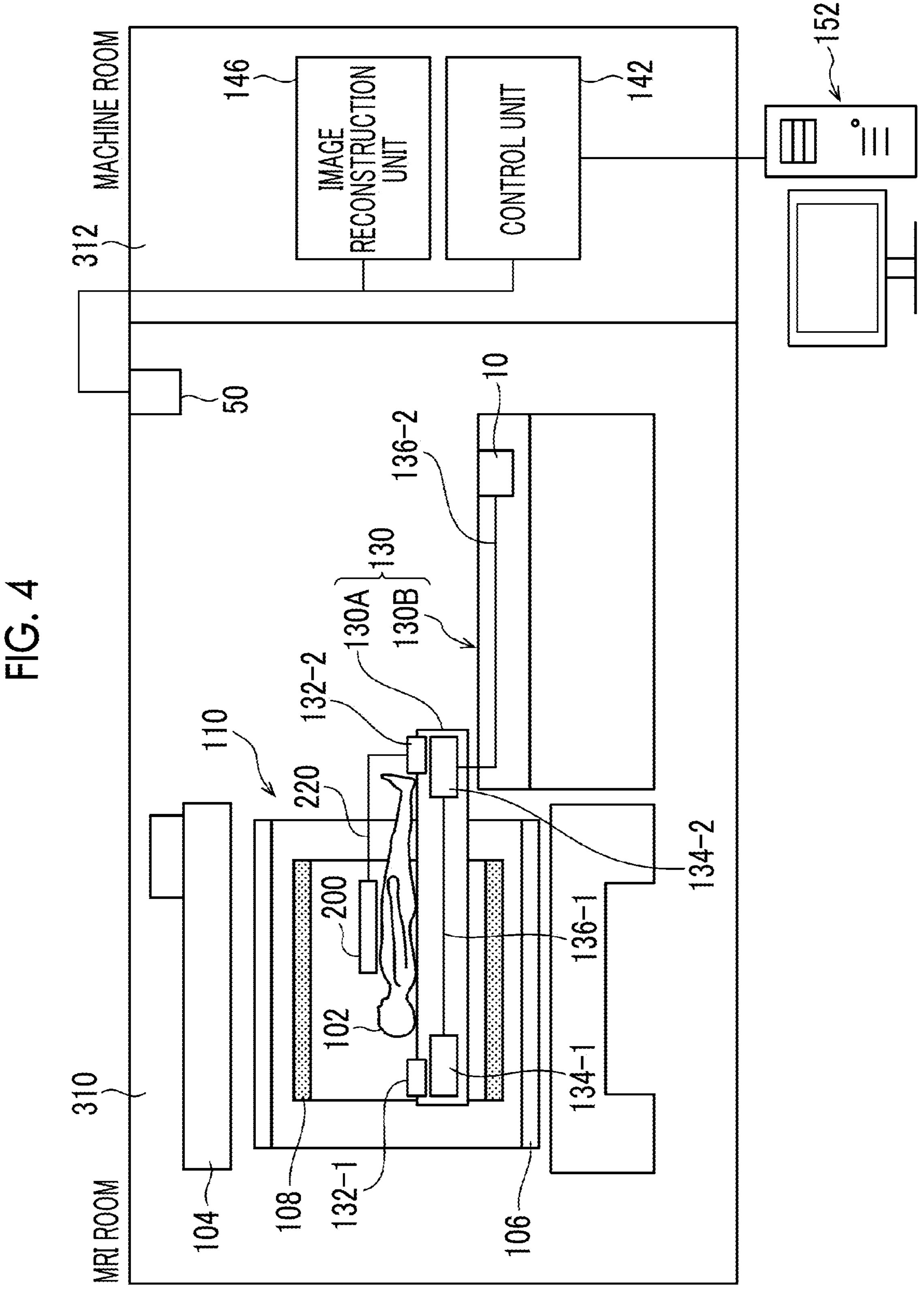
FIG. 4 is an explanatory diagram schematically showing a configuration of the MRI apparatus including a patient table according to an embodiment.

Description of Configuration of MRI Apparatus Including Patient Table According to Embodiment FIG. 4 is an explanatory diagram schematically showing a configuration of the MRI apparatus 100 including the patient table 130 according to the embodiment. The gantry 110 and the patient table 130 are disposed inside an MRI room 310, which is an examination room for MRI examinations. The MRI room 310 is an example of a "room where the gantry is disposed".

Figure 5:
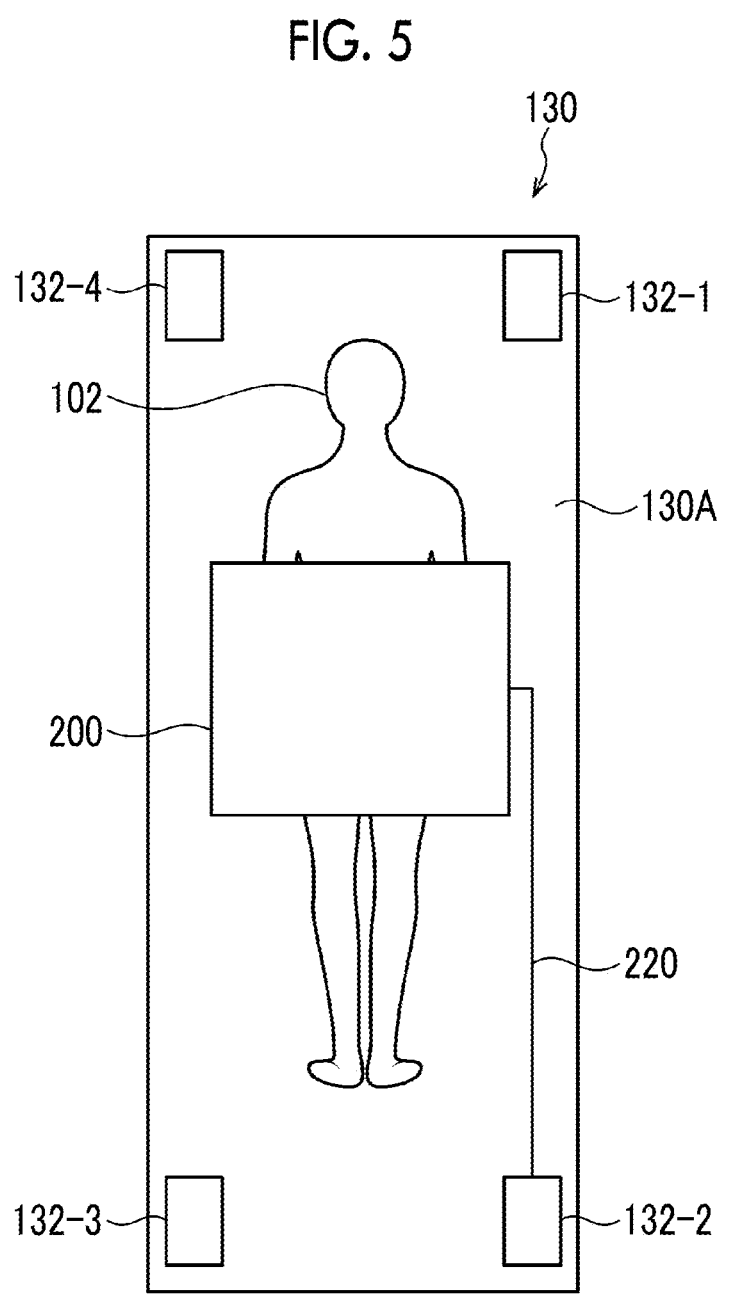

FIG. 5 is a plan view of the patient table 130 and shows a state before the top plate 130A is moved into the bore 120, that is, a state of the initial position of the top plate 130A. The upper direction of FIG. 5 is a direction of the gantry 110. The initial position of the top plate 130A is a predetermined position before the top plate 130A is moved into the imaging space (into the bore 120) and may also be referred to as a home position. The boarding and alighting of the subject 102 on the patient table 130 is performed in a state in which the top plate 130A is at the initial position. The initial position of the top plate 130A may be a position farthest from the gantry 110 in the movement range of the top plate 130A.

Coil ports 132-1, 132-2, 132-3, and 132-4 are disposed on the top plate 130A. A coil port **132-*k* (k=1, 2, 3, and 4) is a connector unit including a connector to which a signal transmission cable 220 of the receive coil unit 200 is connectable. In FIG. 5, an example is shown in which the coil ports 132-*k* are disposed at four corners of the top plate 130A, but the number and the disposition location of the coil ports are not limited to the example of FIG. 5. The coil ports are disposed at one or more locations, preferably at a plurality of locations, on the top plate 130**A.

The signal transmission cable 220 is an electrical cable that transmits the signal of each channel output from the receive coil unit 200. The signal transmission cable 220 may be connected to the receive coil unit 200 via a connector or may be integrated with the receive coil unit 200.

The signal transmission cable 220 of the receive coil unit 200 is connected to any coil port **132-*k* on the top plate 130A. In FIG. 5, an example is shown in which the signal transmission cable 220 is connected to the coil port 132-2 at the lower right, but the signal transmission cable 220 may be connected to another coil port 132-1, 132-3, or 132-4**.

An A/D conversion unit **134-*k* corresponding to each of the coil ports 132-*k* (refer to FIGS. 4 and 7) is provided inside the top plate 130A. The A/D conversion unit 134-*k* may be disposed directly below the corresponding coil port 132-*k*. The A/D conversion unit 134-*k* may be incorporated into the coil port 132-*k***.

A specific configuration example of the A/D conversion unit **134-*k* will be described below with reference to FIG. 6. Each A/D conversion unit 134-*k* comprises an electrical-to-optical (E/O) converter 164 and an optical-to-electrical (O/E) converter 166. In addition, each A/D conversion unit 134-*k* is a signal conversion module comprising a parallel-to-serial (P/S) converter 162 and a serial-to-parallel (S/P) converter 168**.

An optical signal output from the A/D conversion unit **134-*k* is transmitted to an optical wireless unit 10 using an optical cable 136-*k***. The term "optical cable" is synonymous with an optical fiber cable.

The optical wireless unit 10 is an optical communication module that transmits and receives an optical signal via optical wireless communication, and is disposed on the leg portion 130B of the patient table 130 as shown in FIG. 4. The leg portion 130B is a portion that does not move in a state in which the patient table 130 is connected to the gantry 110.

From the viewpoint of suppressing communication failure caused by dust or the like, the optical wireless unit 10 is disposed beneath the top plate 130A in a state before the subject 102 is set up in the imaging space, and the optical wireless unit 10 is disposed at a position that is exposed on the leg portion 130B in a case where the top plate 130A is moved into the gantry 110 in order to set up the subject 102 in the imaging space. The position beneath the top plate 130A refers to a position beneath the top plate 130A in a direction of gravity and is a position overlapping a region of the top plate 130A in plan view.

More specifically, the optical wireless unit 10 is disposed on the upper surface portion of the leg portion 130B at a position that is covered by the top plate 130A in a case where the top plate 130A is at the initial position (home position) before moving into the bore 120, and is configured to be exposed on the leg portion 130B as the top plate 130A moves into the bore 120.

In a case where the top plate 130A is at the initial position, the optical wireless unit 10 is covered by the top plate 130A, and the optical wireless unit 10 is not exposed on a surface of the patient table 130 (in a non-exposed state) (refer to FIG. 5), thereby suppressing the adhesion of dust or the like to the optical wireless unit 10.

On the other hand, in a case where the top plate 130A is moved into the gantry 110 in order to set up the subject 102, the optical wireless unit 10 is exposed by the movement, thereby enabling optical wireless communication.

Regarding the disposition location of the optical wireless unit 10 on the leg portion 130B, there is some degree of freedom, but in order to enable the early establishment of optical wireless communication due to the movement of the top plate 130A, it is preferable that the optical wireless unit 10 is disposed on the leg portion 130B at the end portion on the side opposite to the gantry 110 (near the rear end portion). The term "end portion" includes an end and surrounding parts. FIG. 4 shows an example in which the optical wireless unit 10 is disposed on the upper surface portion of the leg portion 130B at the end portion on the side opposite to the gantry 110.

The optical cable 136-*k* is disposed inside the top plate 130A and the leg portion 130B and is extended from the A/D conversion unit 134-*k* to the optical wireless unit 10 on the rear end side of the leg portion 130B.

Figure 7:
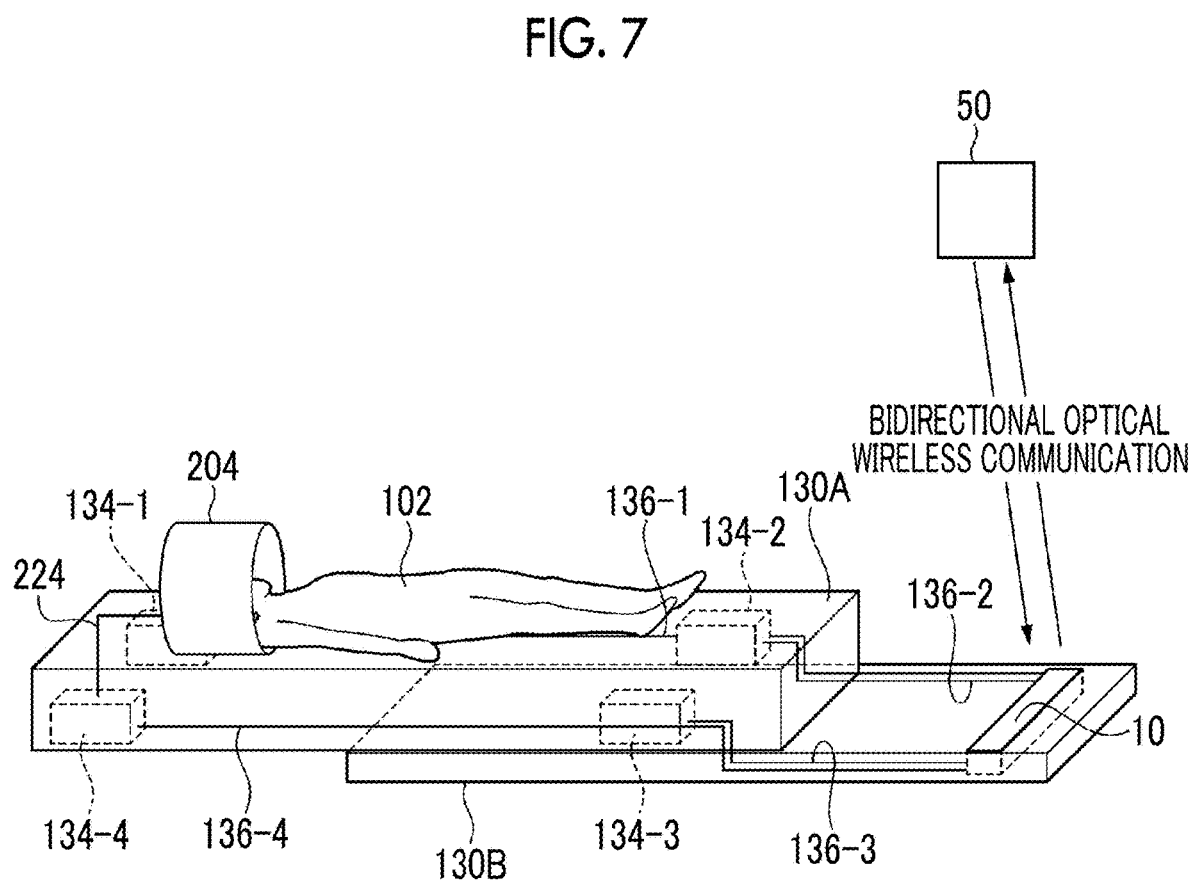

The optical wireless unit 10 is connected to a plurality of A/D conversion units 134-*k* via the optical cables 136-*k* (refer to FIG. 7). In this case, the optical wireless unit 10 comprises a switch for selecting a signal to be activated from the plurality of A/D conversion units 134-*k*.

The optical wireless unit 50 that forms an optical link with the optical wireless unit 10 is disposed on a ceiling of the MRI room 310 or a wall surface of the MRI room 310. The optical wireless unit 50 is an optical communication module that transmits and receives an optical signal via optical wireless communication, similar to the optical wireless unit 10, and functions as an optical controller. A control unit 142 and an image reconstruction unit 146 of the MRI apparatus 100 are disposed in a machine room 312 and are connected to the optical wireless unit 50. The optical wireless unit 10 is an example of a "first optical wireless unit", and the optical wireless unit 50 is an example of a "second optical wireless unit".

The control unit 142 includes a processor that generates a control signal and a multiplexer. The processor may be configured using, for example, a field programmable gate array (FPGA). The processor is not limited to the FPGA and may be configured using another programmable integrated circuit (IC) or digital signal processor (DSP), a combination thereof, or the like. The control unit 142 is connected to a console 152. The console 152 may include a computer that functions as the controller 140 and the operation unit 150 shown in FIG. 2.

Configuration Example of A/D Conversion Unit

Figure 6:
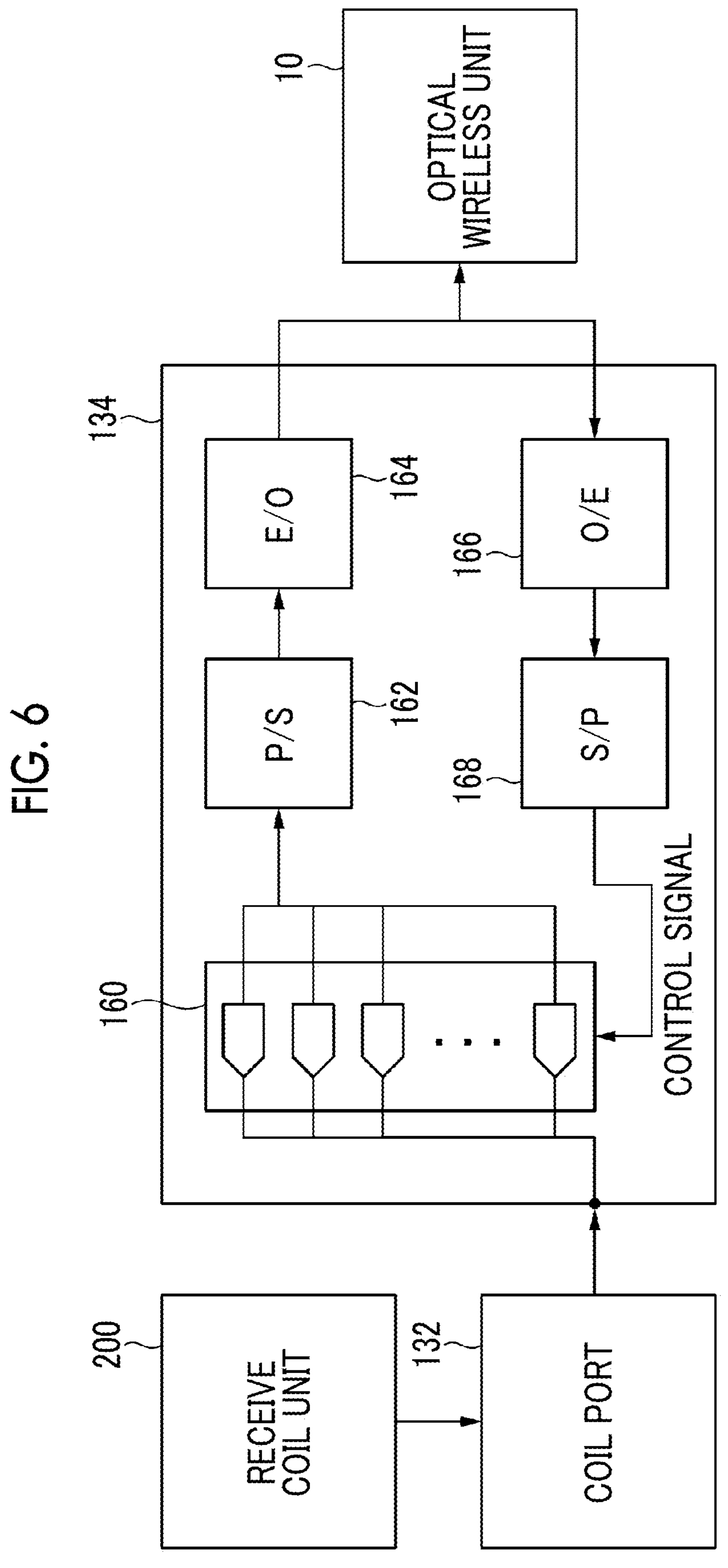
FIG. 6 is a block diagram showing a configuration example of an A/D conversion unit.

Since the configurations of the A/D conversion units 134-*k* are common, descriptions will be provided using an A/D conversion unit 134 in FIG. 6. Additionally, since the configurations of the coil ports 132-*k* are also common, descriptions will be provided using a coil port 132 in FIG. 6. A receive coil unit 204 or other types of receive coil units can be connected to the coil port 132, not just the receive coil unit 200.

FIG. 6 is a block diagram showing a configuration example of the A/D conversion unit 134. The A/D conversion unit 134 includes an A/D converter 160, the P/S converter 162, the E/O converter 164, the O/E converter 166, and the S/P converter 168. The A/D conversion unit 134 is an example of a "signal conversion unit". The E/O converter 164 is an example of an "electrical-to-optical converter".

The A/D converter 160 includes a plurality of A/D converters corresponding to the number of channels of the receive coil unit 200. The A/D converter 160 converts the analog signal received from the receive coil unit 200 through the coil port 132 into digital signal data. The A/D conversion unit 134 may comprise a decimator (not shown) that thins out the digital signal data converted by the A/D converter 160. The P/S converter 162 performs serialization (P/S conversion) for optical transmission. The P/S converter 162 may include a multiplexer and an encoding function. The E/O converter 164 converts the serialized signal data into an optical signal.

The optical signal output from the E/O converter 164 is transmitted to the optical wireless unit 10, is converted into an optical wireless signal by the optical wireless unit 10, and is transmitted to the optical wireless unit 50.

In addition, the optical wireless unit 10 receives the optical wireless signal transmitted from the optical wireless unit 50 and transmits the received signal to the A/D conversion unit 134. The signal received by the optical wireless unit 10 from the optical wireless unit 50 includes, for example, control signals for the A/D converter 160 and the like.

The optical signal transmitted from the optical wireless unit 10 to the A/D conversion unit 134 is converted into an electrical signal by the O/E converter 166. The S/P converter 168 performs deserialization (S/P conversion) of the O/E converted signal. The control signal for each channel output from the S/P converter 168 is transmitted to each control destination, and the operations of the A/D converter 160, the receive coil unit 200, and the like are controlled.

Overview of Bidirectional Optical Wireless Communication

FIG. 7 is an explanatory diagram of bidirectional optical wireless communication using the optical wireless units 10 and 50. In FIG. 7, an example is shown in which the receive coil unit 204 for the head is used instead of the receive coil unit 200. In FIG. 7, the coil port 132-*k* is not shown. The receive coil unit 204 is connected to the A/D conversion unit 134-4 via a signal transmission cable 224. The signal obtained from the receive coil unit 204 is digitized by the A/D conversion unit 134-4 and converted into an optical signal. The optical signal output from the A/D conversion unit 134-4 is transmitted to the optical wireless unit 10 via the optical cable 136-4, is modulated into an optical wireless signal by the optical wireless unit 10, and is transmitted from the optical wireless unit 10 via optical wireless communication.

The optical wireless unit 50 receives the optical wireless signal transmitted from the optical wireless unit 10, converts the received signal into an electrical signal, and transmits the electrical signal to the image reconstruction unit 146. Additionally, the optical wireless unit 50 converts the control signal output from the control unit 142 into an optical signal and transmits the optical signal via optical wireless communication.

The optical signal transmitted from the optical wireless unit 50 is received by the optical wireless unit 10, and the signal is transmitted from the optical wireless unit 10 to the A/D conversion unit 134-4 via the optical cable 136-4. The operation of the A/D conversion unit 134-4 is controlled by a control signal received via the optical wireless unit 10. In addition, the operation of the receive coil unit 204 is controlled by a control signal received via the optical wireless unit 10.

The same applies to the other A/D conversion units 134-1, 134-2, and 134-3, and the A/D conversion units 134-1, 134-2, and 134-3 in a case where the receive coil unit is connected transmit and receive the optical signals to and from the optical wireless unit 10 via the optical cables 136-1, 136-2, and 136-3, respectively.

Overview of Operation of MRI Apparatus 100

An overview of the operation of the MRI apparatus 100 using the optical wireless units 10 and 50 (steps 1 to 11) is as follows. Here, a case where the patient table 130 is a movable dockable patient table is exemplified.

[Step 1] The patient table 130 is docked with the gantry 110.

[Step 2] The subject 102 is placed on the top plate 130A and moved to the imaging region.

[Step 3] The optical wireless unit 10 is exposed on the leg portion 130B by the movement of the top plate 130A, and a link (optical wireless communication connection) between the optical wireless units 10 and 50 is established. The optical wireless communication technology applied may be, for example, light fidelity (LiFi). LiFi is a technology that realizes wireless bidirectional communication by modulating light at a high speed. LiFi can also support optical communication using not only visible light but also near-infrared light and can avoid the influence of electromagnetic interference as compared with wireless communication using radio waves, thereby enabling high-speed and stable communication.

[Step 4] A control signal is output from the control unit 142 in accordance with the receive coil unit and the parameter input or selected by the console 152.

[Step 5] The control signal output from the control unit 142 is optically wirelessly transmitted to the optical wireless unit 10 via the optical wireless unit 50.

[Step 6] The optical wireless unit 10 that has received the control signal transmits the control signal to the A/D conversion unit 134-*k* to which the receive coil unit 200 to be activated is connected. Here, as an example, a case where the control signal is transmitted to the A/D conversion unit 134-2 to which the receive coil unit 200 to be activated is connected will be described.

[Step 7] By executing the imaging pulse sequence, the biological signals (NMR signals) of the plurality of channels acquired by the receive coil unit 200 are input to the A/D conversion unit 134-2 inside the top plate 130A via the existing signal transmission cable 220, a connector (not shown), and the coil port 132-2.

[Step 8] The A/D converter 160, the P/S converter 162, and the E/O converter 164 in the A/D conversion unit 134-2 are operated by the control signal received from the optical wireless unit 10 to perform the A/D conversion, the P/S conversion, and the E/O conversion of each signal, and then the signal is transmitted to the optical wireless unit 10 via the optical cable 136-2 as an optical signal.

[Step 9] In the optical wireless unit 10, the activated signal received from the A/D conversion unit 134-2 to which the receive coil unit 200 is connected is converted into an optical wireless signal and transmitted to the optical wireless unit 50.

[Step 10] The optical wireless unit 50 performs O/E conversion on received data, and the data is transmitted from the optical wireless unit 50 to the image reconstruction unit 146.

[Step 11] The image reconstruction unit 146 performs processing of reconstructing an image from the received data and provides the image to the console 152. In this way, an MRI image, which is the reconstructed image, is displayed on a display device of the console 152.

Example of Control Signal Received by A/D Conversion Unit 134 from Optical Wireless Unit 10

For example, signals listed in [1] to [5] below are serialized and transmitted from the optical wireless unit 50 to the optical wireless unit 10, and the signals are restored (S/P conversion) by the S/P converter 168 in the A/D conversion unit 134 and then transmitted to each control destination.

[1] A sampling clock for the A/D converter 160 synchronized with an RF irradiation signal

[2] A control signal for the operating setting of the A/D converter 160

[3] A control signal for the setting of digital signal processing including decimation and encoding

[4] A control signal for the gain setting of a variable gain amplifier (VGA)

[5] A decoupler signal of the receive coil unit 200

Although not shown, the A/D conversion unit 134 comprises a VGA and a buffer. The control signal for the gain setting of the VGA is distributed to each VGA via the buffer after being restored by the S/P converter 168. Additionally, the decoupler signal of the receive coil unit 200 is restored by the S/P converter 168 and then distributed by a fan-out buffer, thereby performing decoupling control of each coil element 200-*j*.

Regarding Disposition Location of Optical Wireless Unit 10

In FIGS. 4 and 7, an example has been described in which the optical wireless unit 10 is disposed on the rear end side of the upper surface portion of the leg portion 130B, but the shape, the disposition location, and the number of the optical wireless unit 10 are not limited to the examples shown in FIGS. 4 and 7.

Figure 8:
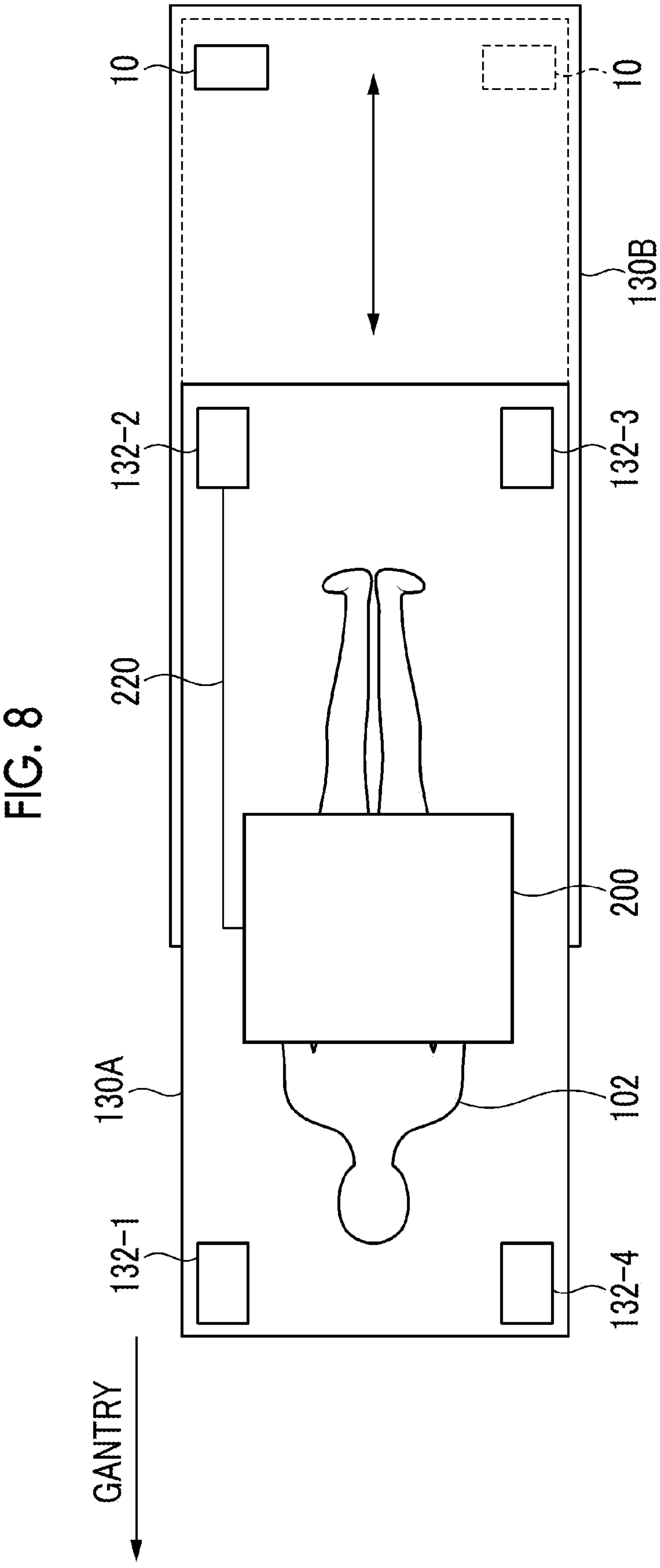
FIG. 8 is a plan view showing a disposition example of the optical wireless unit.

FIG. 8 is a plan view showing a disposition example of the optical wireless unit 10. The optical wireless unit 10 is disposed on the part of the leg portion 130B at a position that is hidden beneath the top plate 130A in a case where the top plate 130A is at the initial position and that is exposed on the leg portion 130B as the top plate 130A moves into the gantry 110. That is, the optical wireless unit 10 is disposed at a position that overlaps the top plate 130A, which is at the initial position, in plan view and that does not overlap the top plate 130A (that is outside the region of the moved top plate 130A) in a case where the top plate 130A is moved into the gantry 110. As an example of the disposition location satisfying such conditions, as shown in FIG. 8, the optical wireless unit 10 is disposed on the upper surface portion of the leg portion 130B at a position that is close to an end (rear end) on the side opposite to the gantry 110 and that is exposed by the movement of the top plate 130A.

In a case where a long side direction (longitudinal direction) of the top plate 130A, which is substantially rectangular in plan view, is defined as a Z-axis direction and a short side direction (lateral direction) is defined as an X-axis direction, and in a case where a gantry 110 side of both ends of the patient table 130 in the Z-axis direction is defined as a front end and the side opposite to the gantry 110 (a side away from the gantry 110) is defined as a rear end, the optical wireless unit 10 may be disposed at a plurality of locations of the upper surface portion on the rear end side of the leg portion 130B that supports the top plate 130A. The bidirectional arrows parallel to the Z-axis direction shown in FIG. 8 indicate the movement of the top plate 130A.

Example of Plurality of Receive Coil Units Connected to Coil Ports

Figure 9:
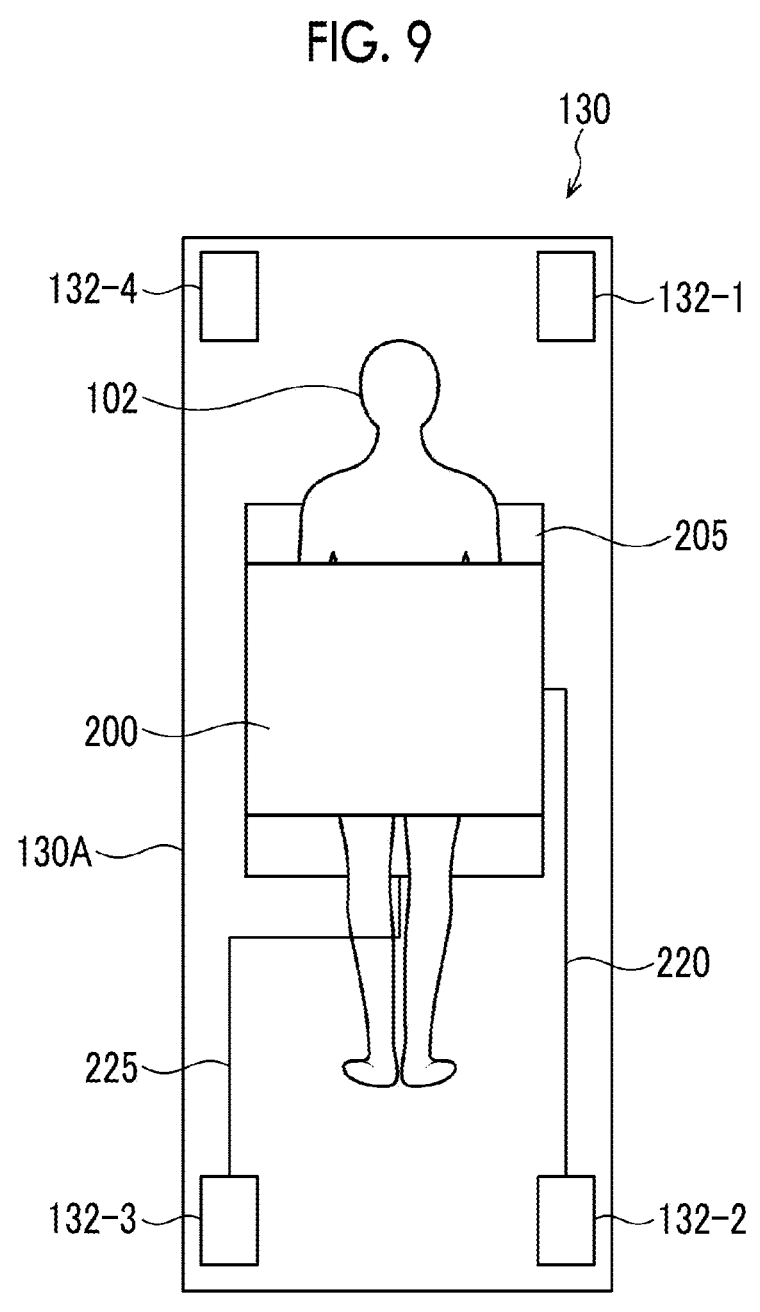

In the MRI apparatus 100, a plurality of receive coil units may be used for the subject 102. FIG. 9 is a plan view showing an example of a case where a plurality of receive coil units 200 and 205 are connected to the coil ports 132-2 and 132-3. In FIG. 9, the receive coil unit 200 for the abdomen and the receive coil unit 205 for the spine are illustrated, but the present disclosure is not limited to the combination thereof. In addition, three or more receive coil units may be used.

For the configuration shown in FIG. 9, elements common to those in FIG. 5 are denoted by the identical reference numerals, and repetitive descriptions will not be repeated. A signal transmission cable 225 of the receive coil unit 205 is connected to, for example, the coil port 132-3.

In a case where the plurality of receive coil units 200 and 205 are connected to the coil ports 132-2 and 132-3, a plurality of activated signals are selected by the optical wireless unit 10, and the signals obtained from each of the receive coil units 200 and 205 are serialized (or multiplexed) and transmitted via optical wireless communication.

Figure 10:
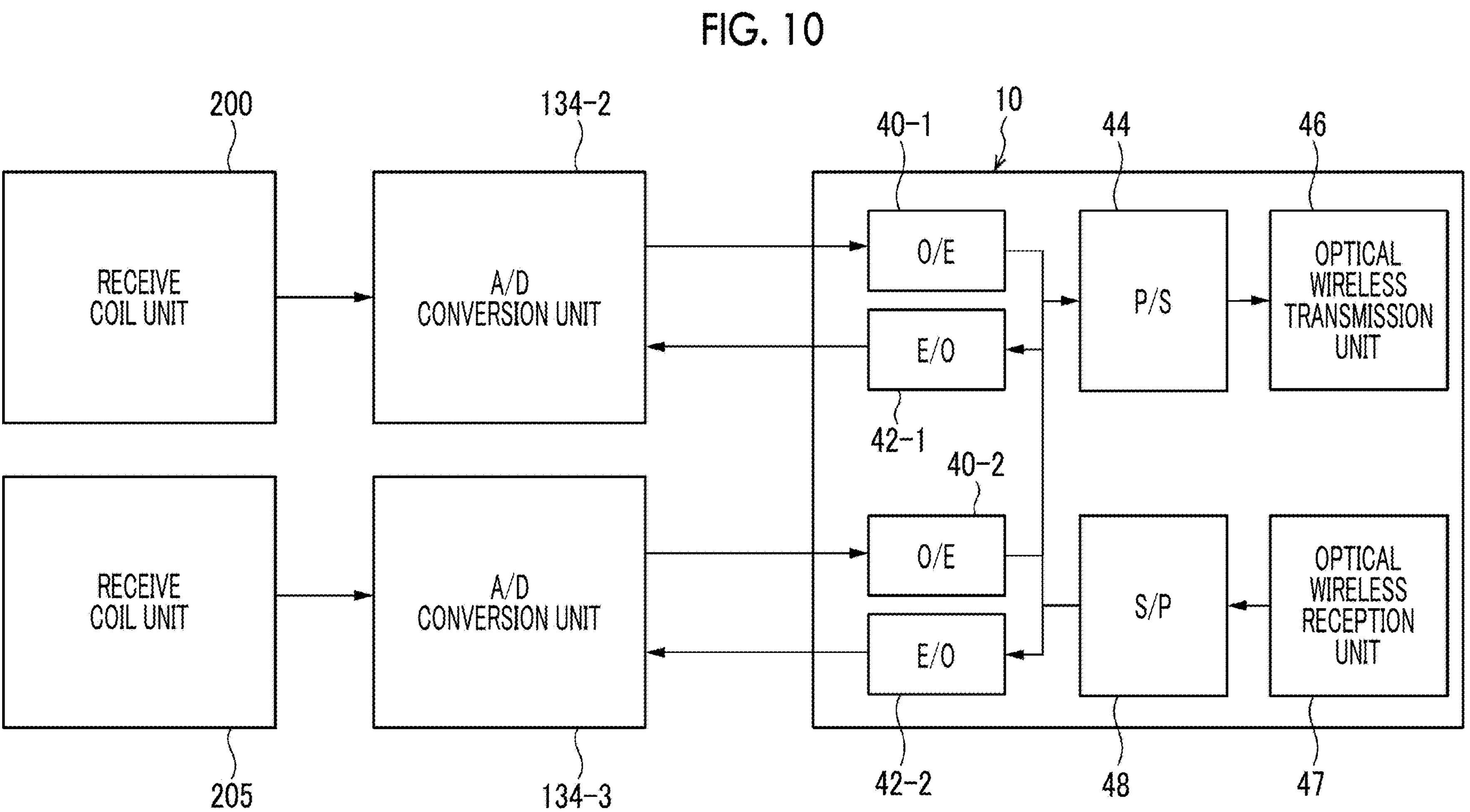
FIG. 10 is a block diagram showing an example of the optical wireless unit that is connectable to the plurality of receive coil units.

FIG. 10 is a block diagram showing an example of the optical wireless unit 10 that is connectable to the plurality of receive coil units 200 and 205. The optical wireless unit 10 comprises, for example, a plurality of O/E converters 40-1 and 40-2, a plurality of E/O converters 42-1 and 42-2, a P/S converter 44, an optical wireless transmission unit 46, an optical wireless reception unit 47, and an S/P converter 48. The optical wireless transmission unit 46 includes a light source, such as a light-emitting diode, and an optical modulator. The optical wireless reception unit 47 includes an optical sensor, such as a photodiode, and an amplification circuit. In FIG. 10, a configuration is shown in which two O/E converters 40-1 and 40-2 and two E/O converters 42-1 and 42-2 are provided, but a configuration may be employed in which two or more O/E converters and two or more E/O converters are provided in accordance with the number of connectable receive coil units.

An overview of the operation (steps 201 to 211) in a case where the plurality of receive coil units 200 and 205 are connected to the coil ports 132-2 and 132-3 is as follows.

[Step 201] First, the plurality of receive coil units 200 and 205 are connected to the plurality of coil ports 132-2 and 132-3 on the top plate 130A. As a result, the plurality of receive coil units 200 and 205 are connected to the corresponding A/D conversion units 134-2 and 134-3, respectively.

[Step 202] Next, the receive coil units 200 and 205 to be activated are selected by the console 152, and the top plate 130A on which the subject 102 is placed is moved into the bore 120. The optical wireless unit 10 is exposed on the leg portion 130B by the movement of the top plate 130A, and communication connection between the optical wireless units 10 and 50 is established.

[Step 203] The control signal is output from the control unit 142 to each of the plurality of activated receive coil units 200 and 205 in accordance with the selection from the console 52.

[Step 204] The control signal output from the control unit 142 is optically wirelessly transmitted to the optical wireless unit 10 via the optical wireless unit 50.

[Step 205] The optical wireless unit 10 receives the control signal transmitted via optical wireless communication from the optical wireless unit 50 using the optical wireless reception unit 47 and performs deserialization of the received control signal using the S/P converter 48. The S/P converter 48 distributes the control signal for each of the receive coil units 200 and 205 and transmits the control signals to the E/O converters 42-1 and 42-2.

[Step 206] The control signals for the receive coil units 200 and 205 are subjected to E/O conversion by the E/O converters 42-1 and 42-2 and are transmitted to the A/D conversion units 134-2 and 134-3 via the optical cables 136-2 and 136-3, respectively. In this way, the control signals are transmitted to all of the plurality of A/D conversion units 134-2 and 134-3 to which the activated receive coil units 200 and 205 are connected.

[Step 207] The A/D conversion units 134-2 and 134-3 perform O/E conversion on the respective received control signals, operate devices such as the A/D converter 160 in accordance with the control signals, and digitize the biological signals obtained from the corresponding receive coil units 200 and 205. That is, similar to the above-mentioned steps 7 and 8, the A/D converters 160, the P/S converters 162, and the E/O converters 164 in the A/D conversion units 134-2 and 134-4 are operated by the control signals received from the optical wireless unit 10 to perform the A/D conversion, the P/S conversion, and the E/O conversion of the signal of each channel. In this way, the signal data obtained from the plurality of receive coil units 200 and 205 is converted into optical signals by the A/D conversion units 134-2 and 134-3 and is transmitted to the optical wireless unit 10 via the optical cables 136-2 and 136-3.

[Step 208] The optical wireless unit 10 receives the optical signals transmitted from the plurality of A/D conversion units 134-2 and 134-3 and performs P/S conversion by the P/S converter 44 after O/E conversion by the O/E converters 40-1 and 40-2.

[Step 209] The optical wireless transmission unit 46 of the optical wireless unit 10 converts the P/S-converted data into optical wireless data and transmits the optical wireless data to the optical wireless unit 50.

[Step 210] The optical wireless unit 50 performs O/E conversion and further performs S/P conversion on the received data, and then the data is transmitted from the optical wireless unit 50 to the image reconstruction unit 146 in the same manner as in step 10.

[Step 211] The image reconstruction unit 146 performs processing of reconstructing an image from the received data and provides the image to the console 152.

Procedure of MRI Imaging

Here, an overall flow of MRI imaging will be described. FIG. 11 is a flowchart showing a procedure of MRI imaging. An overview of the procedure of MRI imaging (steps S310 to S321) is as follows.

In step S310, a technician and a patient enter the MRI room 310. The technician is a diagnostic radiologist. The patient is the subject 102 undergoing an MRI examination.

In step S311, the patient lies on the top plate 130A on the patient table 130.

In step S312, the technician adjusts the positions of the patient and the receive coil unit.

In step S313, the top plate 130A is moved to a magnetic field center of the gantry 110.

In step S314, the technician leaves the MRI room 310 and enters a control room.

In step S315, the technician operates the console 152 from the control room to capture an alignment image and confirms whether there is a problem with the patient and the coil setup position. The patient and the coil setup position include a position of the patient and a position of the receive coil unit worn by the patient. In a case where the technician determines that there is a problem in the confirmation process of step S315, the process returns to step S312, and the technician adjusts the positions of the patient and the receive coil unit.

In a case where the technician determines that there is no problem in the confirmation process of step S315, the process transitions to step S316.

In step S316, the technician starts the main imaging.

In step S317, the technician confirms whether there is a problem with an image output from the main imaging. In a case where the technician determines that there is a problem in the image confirmation process of step S317, the process returns to step S316, and the technician executes the main imaging.

In a case where the technician determines that there is no problem in the image confirmation process of step S317, the process transitions to step S318.

In step S318, the technician enters the MRI room 310.

In step S319, the top plate 130A on which the patient is placed is moved out of the bore 120 and returned onto the leg portion 130B.

In step S320, the technician removes the receive coil unit from the patient and helps the patient alight from the top plate.

In step S321, the technician and the patient leave the MRI room 310, and the examination is completed.

Example of Timing of Optical Wireless Connection

There may be various aspects regarding the timing of the optical wireless connection (optical link) between the optical wireless unit 10 and the optical wireless unit 50. As one of typical examples, a configuration may be employed in which, in a state in which the top plate 130A is at the initial position, that is, in a non-exposed state in which the optical wireless unit 10 is disposed beneath the top plate 130A (hereinafter, referred to as a standby state), the power of the optical wireless unit 10 on a patient table 130 side remains ON, and an optical link is established between the optical wireless unit 10 and the optical wireless unit 50 at a stage where the optical wireless unit 10 is exposed on the leg portion 130B by the movement of the top plate 130A.

In addition, as another example, a configuration may be employed in which the position of the top plate 130A, the state of the patient (subject 102) on the top plate 130A, or the like is detected using a sensor, and the power of the optical wireless unit 10 is turned ON/OFF based on a signal obtained from the sensor. As the sensor, for example, various types of sensors can be used depending on the purpose, such as a position sensor, a proximity sensor, a distance-measuring sensor, a weight sensor, or an image sensor, and a combination of the plurality of types of sensors may be used.

Example of Form in which Sensor that Detects Movement of Top Plate 130A is Provided The patient table 130 may comprise a sensor (not shown) that detects the movement of the top plate 130A. In this case, the patient table 130 comprises a circuit (hereinafter, referred to as a first circuit) (not shown) that operates the optical wireless unit 10 based on a signal obtained from the sensor. The first circuit may include a circuit that turns ON/OFF the power of the optical wireless unit 10 with the signal obtained from the sensor as a trigger.

As an example of a specific operation, in a standby state in which the top plate 130A is at the initial position (home position), the power of the optical wireless unit 10 remains OFF. In a case where the sensor detects the movement of the top plate 130A on which the patient is placed, the first circuit turns ON the power of the optical wireless unit 10 based on the signal from the sensor. Consequently, the optical wireless connection is established between the optical wireless unit 10 and the optical wireless unit 50. That is, the power of the optical wireless unit 10 is turned ON at a time when the top plate 130A is operated from the standby state, and an optical link is established.

After that, in a case where imaging ends and the sensor detects that the top plate 130A has returned onto the leg portion 130B, the first circuit turns OFF the power of the optical wireless unit 10. That is, after imaging ends, the power of the optical wireless unit 10 is turned OFF at a time when the top plate 130A has returned onto the leg portion 130B, and the optical wireless connection is disconnected.

With such a configuration, the power of the optical wireless unit 10 can be automatically turned ON/OFF in conjunction with the operation of the top plate 130A. The timing at which the optical wireless unit 10 is exposed on the leg portion 130B by the movement of the top plate 130A and the timing at which the power of the optical wireless unit 10 is turned ON do not need to be strictly matched and may be offset. That is, the power may be turned ON after the movement of the top plate 130A begins and before the optical wireless unit 10 is exposed, or the power may be turned ON after the optical wireless unit 10 is exposed.

Additionally, similarly, the timing at which the optical wireless unit 10 is hidden (not exposed) beneath the top plate 130A in a case where the top plate 130A is returned onto the leg portion 130B after imaging ends and the timing at which the power of the optical wireless unit 10 is turned OFF do not need to be strictly matched and may be offset.

Example of Form in Which Weight Sensor Is Provided in Top Plate 130A

The patient table 130 may comprise a weight sensor (not shown) that can determine a boarding and alighting state of the subject 102 on the top plate 130A. In this case, the patient table 130 may comprise a circuit (hereinafter, referred to as a second circuit) (not shown) that operates the optical wireless unit 10 based on a signal obtained from the weight sensor. The second circuit may include, for example, a circuit that turns ON/OFF the power of the optical wireless unit 10 with the signal obtained from the weight sensor as a trigger.

As an example of a specific operation, the power of the optical wireless unit 10 remains OFF in a standby state. In a case where the patient mounts the top plate 130A, the weight sensor is turned ON, and the power of the optical wireless unit 10 is turned ON by the second circuit that operates in response to the signal from the sensor. After imaging ends, in a case where the patient alights from the top plate 130A and the weight sensor is turned OFF, the power of the optical wireless unit 10 is turned OFF by the second circuit.

That is, the power of the optical wireless unit 10 is turned ON at a time when the weight sensor detects that the patient has mounted the top plate 130A, and the optical wireless connection is established by the exposure of the optical wireless unit 10. After imaging ends, the optical wireless unit 10 is covered by the top plate 130A through the operation of returning the top plate 130A to the initial position, and then the power of the optical wireless unit 10 is turned OFF at a time when the patient alights from the top plate 130A. With such a configuration, the power of the optical wireless unit 10 can be automatically turned ON/OFF in conjunction with the boarding and alighting operations of the patient on and from the patient table 130.

Description of Form in Which Patient Monitoring Monitor Is Provided in Gantry 110

The gantry 110 may comprise a patient monitoring monitor (not shown) that monitors the patient on the top plate 130A. The patient monitoring monitor may include, for example, a camera, an image processing circuit that processes an image captured by the camera, and a display device that displays the image obtained from the camera and various kinds of information understood from the image. The camera may be disposed on the gantry 110 or may be disposed on the ceiling, the wall surface, or the like of the MRI room 310.

The image processing circuit may include a processor that executes processing of detecting a target object, such as a patient or a phantom, from the image. The processing of detecting the target object from the image may be processing by artificial intelligence (AI) to which a trained model that has been trained to recognize a region of the target object from the image by using, for example, an object detection algorithm using machine learning is applied.

The MRI apparatus 100 has a function of determining a state in which the patient or the phantom is placed on the top plate 130A by using the patient monitoring monitor, and the patient table 130 may comprise a circuit (hereinafter, referred to as a third circuit) (not shown) that operates the optical wireless unit 10 based on a signal obtained by the patient monitoring monitor. The third circuit may include, for example, a circuit that turns ON/OFF the power of the optical wireless unit 10 with a detection signal of the target object obtained from the patient monitoring monitor as a trigger.

As a specific operation, for example, the power of the optical wireless unit 10 remains OFF in a standby state. Then, in a case where the patient mounts the top plate 130A, the phantom is placed on the top plate 130A, or the like, and a state in which the patient or the phantom is placed on the top plate 130A is observed through the patient monitoring monitor, the power of the optical wireless unit 10 is turned ON by the third circuit that operates in response to an observation result.

After imaging ends, in a case where a state in which the patient or the phantom has alighted from the top plate 130A is observed through the patient monitoring monitor, the power of the optical wireless unit 10 is turned OFF by the third circuit.

That is, the power of the optical wireless unit 10 is turned ON at a time when the patient or the phantom on the top plate is detected by the camera for patient monitoring, and the optical wireless connection is established by the exposure of the optical wireless unit 10. After imaging ends, the optical wireless unit 10 is covered by the top plate 130A through the operation of returning the top plate 130A to the initial position, and then the power of the optical wireless unit 10 is turned OFF at a time when the patient is no longer detected by the camera, for example, when the patient alights from the top plate 130A.

Regarding Configuration in which Optical Wireless Unit 50 Also Serves as Light in MRI Room 310

The optical wireless unit 50 may also serve as a lighting fixture (light). For example, by employing a configuration in which a plurality of optical wireless units 50 are disposed on the ceiling of the MRI room 310 and each of the optical wireless units 50 performs visible light communication with the optical wireless unit 10, the optical wireless unit 50 can be used as a light for illumination in the MRI room 310.

In a case where there is an illumination device or another illumination equipment in the gantry 110 in addition to the optical wireless unit 50, the optical signals for visible light communication can be filtered based on a communication speed, thereby enabling communication without interference between light sources.

Regarding Configuration in which Digital Processing Function is Implemented in A/D Conversion Unit 134

The A/D conversion unit 134 may have a digital processing function and may transmit a signal in a communication format suitable for optical wireless communication. The A/D conversion unit 134 comprises, for example, a digital processing circuit that performs processing such as decimation and encoding. The encoding may be, for example, conversion from 8 bits to 10 bits (8b/10b conversion). The A/D conversion unit 134 comprising the digital processing circuit digitizes the analog signal acquired from the receive coil unit using the A/D converter 160 and then thins out the data through decimation. Then, the thinned-out data is encoded (such as 8b/10b conversion) to prevent the occurrence of continuous bits. Through such digital processing, the signal can be adjusted to correspond to a transmission amount and a transmission speed of the optical wireless communication. Specific processing examples will be described below.

For example, in a case where data of 16 bits, 100 Msps (samples per second), and 16 channels is transmitted, in order to achieve an optical wireless signal of 10 Gbps or less, the following equation applies:

$$16\times 100\text{M}\times(1/4)\times(10/8)\times 16=8.0\text{ Gbps}.$$

As shown in the equation, by setting the decimation factor to 4 and encoding to 8b/10b, the specifications can be satisfied.

Example of Patient Table Comprising Plurality of Optical Wireless Units

Figure 12:
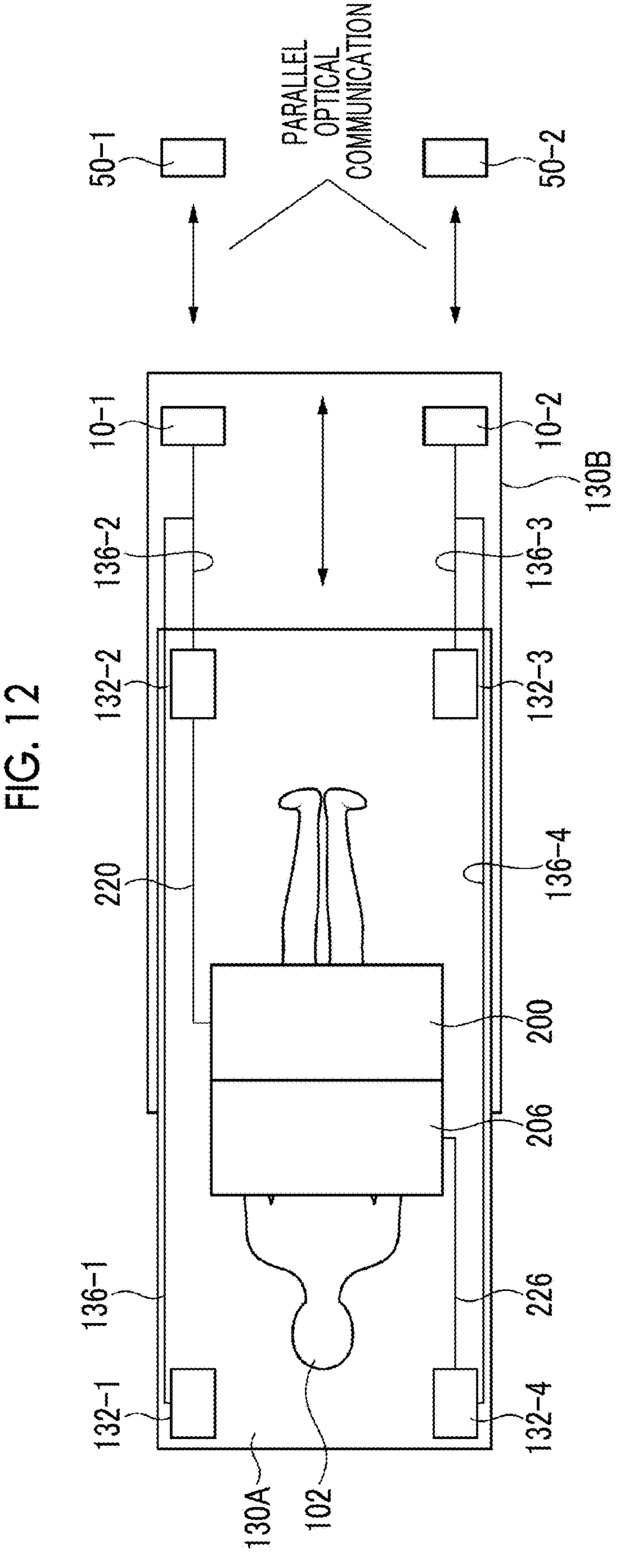
FIG. 12 is an explanatory diagram showing an example of a patient table comprising a plurality of optical wireless units.

FIG. 12 is an explanatory diagram showing an example of a patient table 130 comprising a plurality of optical wireless units 10-1 and 10-2. In the patient table 130 shown in FIG. 12, the plurality of optical wireless units 10-1 and 10-2 are disposed on the upper surface portion of the leg portion 130B. The optical wireless unit 10-1 is connected to the A/D conversion units 134-1 and 134-2 (not shown in FIG. 12, refer to FIG. 7) corresponding to the coil ports 132-1 and 132-2 via the optical cables 136-1 and 136-2.

In addition, the optical wireless unit 10-2 is connected to the A/D conversion units 134-3 and 134-4 (not shown in FIG. 12, refer to FIG. 7) corresponding to the coil ports 132-3 and 132-4 via the optical cables 136-3 and 136-4.

That is, the signals digitized by the A/D conversion units 134-1 and 134-2 are transmitted to the optical wireless unit 10-1, and the signals digitized by the A/D conversion units 134-3 and 134-4 are transmitted to the other optical wireless unit 10-2. The functions of the optical wireless units 10-1 and 10-2 may be the same as the function of the optical wireless unit 10 shown in FIG. 10.

In a case of the example shown in FIG. 12, the signal obtained from the receive coil unit 200 is digitized by the A/D conversion unit 134-2 and is transmitted to the optical wireless unit 10-1. Additionally, the signal obtained from a receive coil unit 206 is digitized by the A/D conversion unit 134-4 and is transmitted to the optical wireless unit 10-2. In this way, large-volume data obtained from the plurality of receive coil units 200 and 206 is transmitted in parallel to fit within the optical wireless data transfer rate.

In addition, a plurality of optical wireless communication units 50-1 and 50-2 may be disposed on the ceiling or the like of the MRI room 310. Similar to the optical wireless unit 50 shown in FIG. 4, each of the optical wireless units 50-1 and 50-2 is connected to the image reconstruction unit 146 and the control unit 142.

The optical wireless connection (optical link) is established between the optical wireless unit 50-1 and the optical wireless unit 10-1, and the optical wireless connection is established between the optical wireless unit 50-2 and the optical wireless unit 10-2, thereby enabling parallel optical communication through each optical link.

Effects of Embodiment

With the patient table 130 comprising the optical wireless unit 10 (or the optical wireless units 10-1 and 10-2) according to the embodiment and the MRI apparatus 100 including the patient table 130, the following effects can be obtained.

(1) In a case where the top plate 130A is at the initial position, the optical wireless units 10, 10-1, and 10-2 are disposed beneath the top plate 130A and are in a non-exposed state, so that it is possible to suppress the adhesion of dust or the like to the optical wireless unit 10. Additionally, in a case where the top plate 130A is moved into the bore 120, the optical wireless units 10, 10-1, and 10-2 are exposed, and optical wireless connection to the optical wireless units 50 disposed on the ceiling or the like of the MRI room 310 becomes possible. As a result, continuous and stable optical wireless communication is possible.

(2) Since the A/D conversion unit 134-*k* is disposed inside the top plate 130A to correspond to the coil port 132-*k* of the top plate 130A, the digitization and the E/O conversion of the signal can be performed near the coil port 132-2, thereby suppressing noise interference and signal loss.

(3) For the configurations of the receive coil units 200, 204, 205, and 206, the signal transmission cables 220, 224, 225, and 226, and the coil port 132-*k*, existing configurations can be used.

(4) Since the data is transmitted through optical wireless modulation by the optical wireless unit 10 disposed on the leg portion 130B, and the data is received by the optical wireless unit 50 and transmitted to the image reconstruction unit 146, this configuration allows for data transmission while avoiding electromagnetic interference. In addition, optical cable wiring is not required between the patient table 130 and the image reconstruction unit 146.

(5) Since the optical cable connection is not required between the patient table 130 and the image reconstruction unit 146, the patient table 130 can be easily configured as a movable patient table (dockable patient table).

(6) By connecting the A/D conversion unit 134-*k* corresponding to each of the plurality of coil ports 132-*k* provided on the top plate 130A to the optical wireless unit 10 via the optical cable 136-*k*, the signal obtained from the activated receive coil unit can be selectively transmitted through optical wireless communication.

(7) With the MRI apparatus according to the present embodiment, the influence of noise components can be suppressed, thereby obtaining a high-quality image.

OTHERS

The present invention is not limited to the above-mentioned embodiment, and various modifications are possible within the scope of the technical concept of the present disclosure without departing from its gist.

EXPLANATION OF REFERENCES

10, 10-1, 10-2: optical wireless unit
40-1, 40-2: O/E converter
42-1, 42-2: E/O converter
44: P/S converter
46: optical wireless transmission unit
47: optical wireless reception unit
48: S/P converter
50, 50-1, 50-2: optical wireless unit
100: MRI apparatus
102: subject
104: static magnetic field generating magnet
106: gradient magnetic field coil
108: RF transmit coil
110: gantry
112: high-frequency magnetic field generator
114: receiver
116: gradient magnetic field power supply
118: sequencer
120: bore
130: patient table
130A: top plate
130B: leg portion
132, 132-1, 132-2, 132-3, 132-4: coil port
134, 134-1, 134-2, 134-3, 134-4: A/D conversion unit
136-1, 136-2, 136-3, 136-4: optical cable
140: controller
142: control unit
146: image reconstruction unit
150: operation unit
152: console
160: A/D converter
162: P/S converter
164: E/O converter
166: O/E converter
168: S/P converter
200, 204, 205, 206: receive coil unit
200-1, 200-2, 200-3, 200-4: coil element
202: decoupling power supply
210-1, 210-2, 210-3, 210-4: decoupling circuit
220, 224, 225, 226: signal transmission cable
310: MRI room
312: machine room
S310 to S321: steps of MRI imaging procedure

What is claimed is:

1. A patient table comprising:
a top plate that moves with a subject placed thereon;
a leg portion that supports the top plate;
a signal conversion unit that is connected to a receive coil unit which receives a signal generated by the subject, the signal conversion unit being disposed inside the top plate and including an A/D converter that converts the signal obtained from the receive coil unit into a digital signal, and an electrical-to-optical converter that converts the digital signal into an optical signal;
an optical cable that is disposed inside the top plate and the leg portion and that transmits the optical signal output from the signal conversion unit; and
an optical wireless unit that is disposed on the leg portion, that is connected to the optical cable, and that transmits the optical signal via optical wireless communication,
wherein the optical wireless unit is disposed at a position that is hidden beneath the top plate in a case where the top plate is at an initial position before moving into an imaging space and that is exposed on the leg portion as the top plate moves into the imaging space.

2. The patient table according to claim 1,
wherein the optical wireless unit is disposed on an upper surface portion of the leg portion.

3. The patient table according to claim 1,
wherein the optical wireless unit is disposed on an upper surface portion of the leg portion at an end portion on a side opposite to the imaging space.

4. The patient table according to claim 1,
wherein the top plate includes a coil port including a connector to which a signal transmission cable of the receive coil unit is connected, and
the signal conversion unit is disposed to correspond to the coil port.

5. The patient table according to claim 4,
wherein the top plate includes a plurality of the coil ports, and the signal conversion unit is provided for each of the plurality of coil ports.

6. The patient table according to claim 1, wherein a plurality of the signal conversion units and a plurality of the optical cables are provided.

7. The patient table according to claim 6, wherein the optical wireless unit includes a switch for selecting a signal to be activated from the plurality of signal conversion units.

8. The patient table according to claim 6, wherein the optical wireless unit includes a circuit that serializes signals obtained from a plurality of the receive coil units connected to the plurality of signal conversion units.

9. The patient table according to claim 1, wherein the signal conversion unit includes a digital processing circuit.

10. The patient table according to claim 9, wherein the digital processing circuit includes a decimator that thins out digitized data.

11. The patient table according to claim 9, wherein the digital processing circuit includes a circuit that performs encoding.

12. The patient table according to claim 1, wherein a plurality of the optical wireless units are provided.

13. A magnetic resonance imaging apparatus comprising:

the patient table according to claim 1;

a gantry that generates a static magnetic field, a gradient magnetic field, and a high-frequency magnetic field in an imaging space;

a second optical wireless unit that performs optical wireless communication with a first optical wireless unit which is the optical wireless unit; and an image reconstruction unit that reconstructs an image based on data of a nuclear magnetic resonance signal acquired via the second optical wireless unit.

14. The magnetic resonance imaging apparatus according to claim 13, wherein the second optical wireless unit is disposed on a ceiling or a wall of a room where the gantry is disposed.

15. The magnetic resonance imaging apparatus according to claim 14, wherein the second optical wireless unit communicates with the first optical wireless unit via visible light communication and also serves as a light for the room.

16. The magnetic resonance imaging apparatus according to claim 13, wherein a plurality of the second optical wireless units are provided.

* * * * *